(12) United States Patent
Conrow

(10) Patent No.: US 6,388,128 B1
(45) Date of Patent: May 14, 2002

(54) STANNANE SYNTHESIS OF PROSTANOIDS

(75) Inventor: Raymond E. Conrow, Crowley, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/787,787

(22) PCT Filed: Sep. 1, 1999

(86) PCT No.: PCT/US99/19976

§ 371 Date: Mar. 23, 2001

§ 102(e) Date: Mar. 23, 2001

(87) PCT Pub. No.: WO00/20386

PCT Pub. Date: Apr. 13, 2000

Related U.S. Application Data

(60) Provisional application No. 60/103,235, filed on Oct. 5, 1998, now abandoned.

(51) Int. Cl.[7] .................... C07C 61/06; C07C 405/00; C07D 307/12
(52) U.S. Cl. .................... 562/503; 549/469; 549/475; 562/465; 562/500; 562/503; 548/468; 548/491
(58) Field of Search ............... 548/468, 491; 549/475, 469; 562/465, 500, 503

(56) References Cited

U.S. PATENT DOCUMENTS 4,777,275 A   10/1988   Campbell et al.

FOREIGN PATENT DOCUMENTS

| DE | 2618861 | 11/1976 |
|----|---------|---------|
| EP | 0295880 A1 | 12/1988 |

OTHER PUBLICATIONS

Ono et al., "Synthesis of Allyl Ester of PGE and the Conversion of the Allyl Ester Moiety into Carboxylic Acid by Chemical Method. A Highly Synthesis of Natural PGE1 and Limaprost", Chemistry Letters, 2095–2098 (1992) XP002128779.

Stork and Isobe, "A General Approach to Prostaglandins via Methylenecyclopentanones. Total Synthesis of (±)–Prostaglandin $F_{2\alpha}$," J. Am. Chem. Soc., 97(16):4745–4746 (Aug. 6, 1975).

Stork & Isobe, "A Simple Total Synthesis of Prostaglandins from 4–cumyloxy–2–cyclopentenone," J. Am. Chem. Soc., 97(21):6260–6261 (Oct. 15, 1975).

Stork and Zhao, "A Stereoselective Synthesis of (Z)–1–IODO–1–Alkenes," Tetrahedron Letters, 30(17):2173–2174 (1989).

Corey et al., "A New Route To Z–Disubstituted Olefins, A Simple Synthesis of Polyunsaturated Fatty Acids by Reiterative Coupling," Tetrahedron Letters, 25(23):2419–2422 (1984).

Dieck et al., "A Palladium–Catalyzed Conjugated Diene Synthesis from Vinylic Halides and Olefinic Compounds," J. Org. Chem., 40(8):1083–1090 (1975).

Kluge et al., "Synthesis of 13–cis–Prostaglandins via a Highly Stereoselective Conjugate Addition with a Functionalized Organcopper Reagent," JACS, 94(26):9256–9258 (1972).

Knochel et al., "The Chemistry of Polyfunctional Organozinc and Copper Reagents," Pure & Appl. Chem., 64(3):361–369 (1992).

Lipshutz et al., "Preparation of Z–vinylstannanes via hydrozirconation of stannylacetylenes," Tetrahedron Letters, 33(40):5861–5864 (1992).

Luthy et al., "Total Synthesis of dl–19–Hydroxyprostaglandin $E_1$ and d1–13–cis15–epi–19–Hydroxyprostaglandin $E_1$", Am. Chem. Soc., 100(19):6211–6217 (1978).

Okamoto et al., "A Highly Efficient Synthesis of Natural PGE3 and 5,6–dihydro PGE3 via Two–Component Coupling Process," Tetrahedron Letters, 30(33):4379–4382 (1989).

Okamoto et al., "A New Efficient Synthesis of the Biologically Potent $PGD_2$–analogue ZK118182," Tetrahedron: Asymmetry, 3(12):1525–1528 (1992).

Okamoto et al., "A New Efficient Synthesis of the Biologically Potent PGD2–Analogue ZK118182," Tetrahedron: Asymmetry, 3(12):1525–1528 (1992).

Primary Examiner—Joseph K. McKane
Assistant Examiner—Sonya Wright
(74) Attorney, Agent, or Firm—Barry L. Copeland

(57) ABSTRACT

The present invention is directed to novel methods of prostanoid synthesis. Specifically, the invention is directed to the addition of alpha chains to prostanoids using cis-alkenylstannane intermediates.

2 Claims, No Drawings

STANNANE SYNTHESIS OF PROSTANOIDS

This application is a 371 of PCT/US99/19976 filed Sep. 1, 1999, which claims priority from Provisional application Ser. No. 60/103,235, filed Oct. 5, 1998.

The present invention is directed to novel methods of prostanoid synthesis. More specifically, the invention is directed to the addition of alpha chains to prostanoids using cis-alkenylstannane intermediates.

BACKGROUND OF THE INVENTION

Naturally occurring prostaglandins are biologically active in a myriad of ways including hormone action, muscular contraction/relaxation, platelet aggregation/inhibition, intraocular pressure reduction and other cellular transduction mechanisms. Prostaglandins are enzymatically produced in nature from arachidonic acid. The arachidonic acid cascade is initiated by the prostaglandin synthase catalyzed cyclization of arachidonic acid to prostaglandin $G_2$ and subsequent conversion to prostaglandin $H_2$. Other naturally occurring prostaglandins are derivatives of prostaglandin $H_2$. A number of different types of prostaglandins have been discovered including A, B, C, D, E, F and I-Series prostaglandins. These descriptions delineate substitution patterns of the various cyclopentane group central to all prostaglandins. Still other naturally occurring derivatives include thromboxane A2 and B2.

Due to their potent biological activity, prostaglandins have been studied for possible pharmaceutical benefit. However, due to potency of these molecules, as well as the ubiquitous presence of these agents and receptors and other biologically responsive tissue sites to their presence, numerous side effects have prevented the exploitation of the naturally occurring prostaglandins. It has also been difficult to pharmaceutically exploit the naturally occurring prostaglandins due to the relatively unstable nature of these molecules. As a result, researchers have been preparing and testing synthetic prostaglandin analogs, also known as "prostanoids," for several decades.

In general, prostanoids can be described generically as consisting of (1) an alpha chain; (2) an omega chain; and (3) a cyclopentane group (or a heterocycle or other ring structure), as shown in formula I.

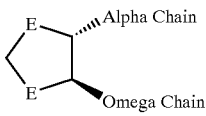

In general, the E groups of the ring structure are independently O, CH—OH, C=O, CH-halogen and $CH_2$ groups. The omega chain has generally consisted of linear carbon backbones of varying lengths. The omega chains have also been of varying degrees of saturation, containing optional hetero-atoms and have terminated with a variety of alkyl and cycloalkyl groups. Alpha chains have consisted of numerous linear moieties and have involved various degrees of saturation. The alpha chains generally consist of a seven carbon chain and generally terminate with a carboxylic acid group or a variety of corresponding esters.

Of particular interest are a set of prostanoids having a double bond at carbons 5 and 6 and an oxygen or carbon at the three position, according to formula II:

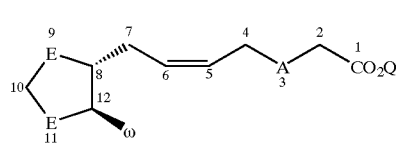

wherein, the E groups are as defined above; A is oxygen or carbon; Q is H or $C_{1-4}$ alkyl: and the omega chain (ω) is generally five to twelve carbons in length with various substitutions including substitutions of heteroatoms within the chain.

As summarized in Scheme A, prostanoids of formula II can be prepared by reacting a methylene ketone 1 with a cis-alkenylcuprate 2 to install the alpha chain and thereby form the cis-alkenyl intermediate 3, wherein X is O, $CH_2$, CH—OH (or CH—O-protected), ω is as defined above, R is generally a nontransferring group, R' is generally a hydroxyl protecting group and Z' is generally a masked carboxyl group.

Scheme A

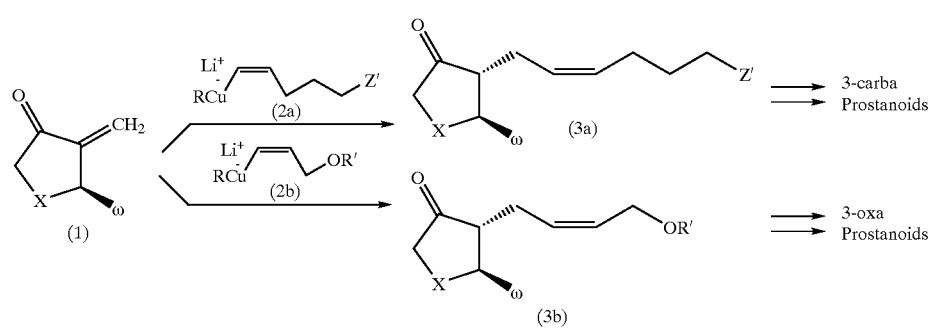

The cis-alkenylcuprate 2a or 2b can be one of several different types known to those skilled in the art. Homocuprates bear two identical carbon groups bonded to copper, only one of which can efficiently form a carbon-carbon bond by transfer from copper, the remaining group being by definition the nontransferring group R. Heterocuprates bear two different carbon groups bonded to copper, one of which (R) has a low tendency to form a carbon-carbon bond compared with the transferring group, in this case the cis-alkenyl group. Higher-order cuprates contain a metal cyanide salt, typically LiCN. Lower-order cuprates do not contain metal cyanide salts but can contain other components capable of modifying reactivity, for example, a trialkylphosphine. The cis-alkenylcuprates of formulas 2a and 2b are optionally associated with a metal cyanide salt or other component. See, generally, Lipshutz, *Organic Reactions*, volume 41, page 135 (1992).

Stork and Isobe, *J. Am. Chem. Soc.*, volume 97, page 4745 (1975), disclose a method of preparing racemic 3-carba prostanoids as shown in Scheme A, wherein X is $CHOCH_2Ph$ (in the rel-R configuration), ω is trans-$CH=CHCH(OCH_2OCH_2Ph)$-n-$C_5H_{11}$, Z' is $CH_2OCH(Me)$ OEt, and the cis-alkenyl cuprate 2a is the lower-order homocuprate cis-$(EtOCH(Me)O(CH_2)_4CH=CH)_2CuLi.PBu3$. The cis-alkenylcuprate 2a was prepared from the cis-iodoalkene cis-$EtOCH(Me)O(CH_2)_4CH=CHI$ by lithium-iodine exchange with tert-butyllithium, forming the intermediate cis-alkenyllithium compound cis-$EtOCH(Me)O(CH_2)_4CH=CHLi$, which was then reacted with CuI—$PBu_3$ complex to yield 2a.

Sato, *Tetrahedron: Asymmetry*, volume 3, page 1525 (1992), discloses a method of preparing nonracemic 3-oxa prostanoids as shown in Scheme A, wherein X is $CHOSiMe_2t$-Bu (in the R configuration), ω is trans-$CH=CHCH(OSiMe_2t$-Bu)-cyclo-$C_6H_{11}$ (in the S configuration), R' is $CH(Me)OEt$, and the cis-alkenylcuprate 2b is the higher-order heterocuprate cis-$EtOCH(Me)OCH_2CH=CHCu(2$-thienyl$)Li.LiCN$. The cis-alkenylcuprate 2b was prepared from the cis-iodoalkene cis-$EtOCH(Me)OCH_2CH=CHI$ by lithium-iodine exchange with tert-butyllithium, forming the intermediate cis-alkenyllithium compound cis-$EtOCH(Me)OCH_2CH=CHLi$, which was then reacted with (2-thienyl)Cu(CN)Li to yield 2b.

The cis-iodoalkene to cis-alkenyllithium to cis-alkenylcuprate sequence employed in the foregoing examples has several disadvantages. The preparation of cis-iodoalkenes typically involves reaction of a 1-iodoalkyne with diimide, which is not suitable for large scale work and always produces some 1-iodoalkane; see Luthy, *J. Am. Chem. Soc.*, volume 100, page 6211 (1978). Other methods of preparing cis-iodoalkenes give variable amounts of the trans isomer, see Dieck, *J. Org. Chem.*, volume 40, page 1083 (1975), and Stork and Zhao, *Tetrahedron Letters*, volume 30, page 2173 (1989). The reagent of choice for converting the cis-iodoalkene to the cis-alkenyllithium has been tert-butyllithium, which is pyrophoric and not suitable for large scale work. This conversion must be performed at low temperature, typically −60° C. or below, in order to realize good yields.

Transmetalation methods have been described in the art. For example, U.S. Pat. No. 4,777,275 (Campbell et al.) discloses a direct tin-to-copper transmetalation. In that disclosure, a trans-alkenylstannane is directly converted to a trans-alkenylcuprate, which is used for the addition of a trans omega chain to a prostanoid.

A need has arisen, therefore, to develop superior synthetic methods for the preparation of the various prostanoids of interest, in greater yields.

SUMMARY OF THE INVENTION

The present invention is directed to methods of prostanoid synthesis. More specifically, the invention is directed to methods involving cis-alkenylstannanes for prostanoid alpha chain addition.

The use of cis-alkenylstannanes obviates problems existing with traditional synthetic methods involving treatment of cis-iodoalkenes with alkyllithiums to form cis-alkenyllithiums, which are then converted to cis-alkenylcuprates. The avoidance of the cis-iodoalkene and cis-alkenyllithium intermediates minimizes unwanted side products and also allows for greater yield of key intermediates useful in prostanoid synthesis.

Preferred methods of the present invention employ the novel intermediate synthesis of the present invention in the synthesis of 3-oxa prostanoids.

DETAILED DESCRIPTION OF THE INVENTION

The present invention is directed to novel methods of prostanoid synthesis. More specifically, the present invention is directed to methods of improved prostanoid alpha chain addition to form prostanoids of formula III:

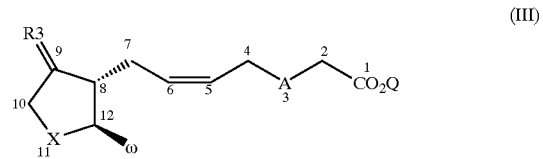

(III)

wherein,

X is O, $CH_2$, C=O, or CH—$OR^4$ in either configuration, or CH-halogen (F, Cl, Br, I) in either configuration;

A is $CH_2$ or O;

Q is H or $C_{1-4}$ alkyl;

R3 is H and one of: H, $OR^4$, halogen, in either configuration, or, R3 is =O (i.e., carbonyl);

$R^4$ is H, alkyl, acyl, or $Si(R^6)_3$, wherein $R^6$ is independently $C_{1-4}$ alkyl or phenyl;

provided that when R3 is =O, X is not CH-halogen, and when R3 is H and halogen, X is not C=O;

ω is

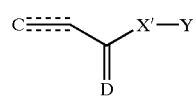

wherein:

---- is an optional bond;

D is H and one of: H, F or $OR^4$, in either configuration; or D is =O (i.e., carbonyl);

$X^1$ is $(CH_2)_m$ or $(CH_2)_mO$, wherein m is 1 to 6; or X' is CH—OH; and

Y is a phenyl ring optionally substituted with alkyl, halo, trihalomethyl, alkoxy, acyl, acyloxy, amino, alkylamino, acylamino, or hydroxy; or Y is $C_{1-6}$ alkyl or $C_{3-8}$ cycloalkyl, optionally substituted with $C_{1-6}$ alkyl, or $X^1-Y$ is $(CH_2)_pY'$; wherein p is 0 to 6; and

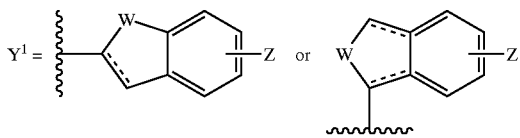

wherein:

W is $CH_2$, $S(O)_q$, $NR^5$, $CH_2CH_2$, $CH=CH$, $CH_2O$, $CH_2S(O)_q$, $CH=N$, or $CH_2NR^5$;

wherein q is 0 to 2, and $R^5$ is H, alkyl, or acyl;

Z is H, alkyl, alkoxy, acyl, acyloxy, halo, trihalomethyl, amino, alkylamino, acylamino, or hydroxy; and ---- is an optional bond; or $X'-Y$ is $C_{1-6}$ alkyl, or $C_{3-8}$cycloalkyl.

Preferred prostanoids synthesized with the methods of the present invention are those of formula III having an ω chain consisting of:

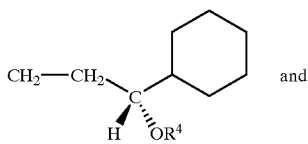

and

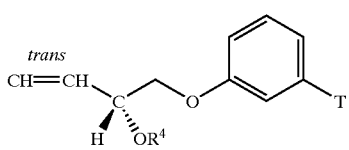

wherein T is $CF_3$ or Cl, and $R^4$ is defined as above. Most preferred are those compounds wherein $^4$ is hydrogen.

The improved alpha addition methods of the present invention are illustrated in Scheme B.

Scheme B

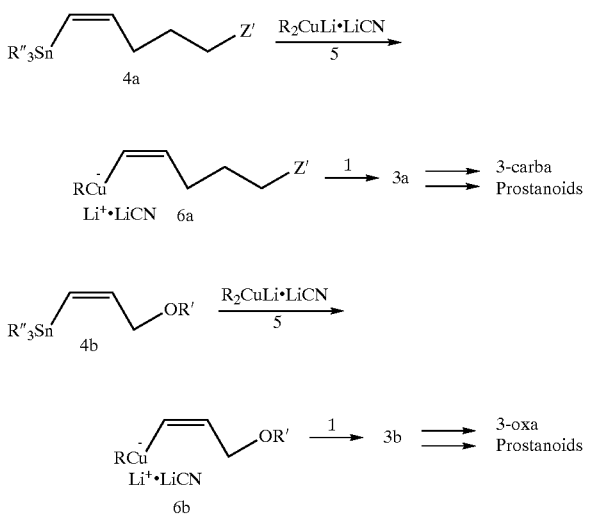

wherein X is O, $CH_2$, CH—OH (or CH—O-protected), and 1, 3a, 3b, are defined as is above.

The cis-alkenylcuprate 6a or 6b is prepared by transmetalation of a cis-alkenylstannane 4a or 4b, respectively, by reaction with a cuprate reagent 5. The R groups of 5 are chosen so that the transmetalation of 4 to 6 proceeds efficiently, and so that in the subsequent reaction of 6 with 1, the R group of 6 is a nontransferring group, for example an alkyl group. The tin-to-copper transmetalation reaction can be performed in several different ways. For example, dilithium (dimethyl)cyanocuprate (5, R is methyl) can be reacted with the cis-alkenylstannane 7 in a solvent such as tetrahydrofuran, diethyl ether, an aromatic hydrocarbon or mixtures thereof. This reaction proceeds efficiently at a temperature of about 0 to 25° C. The resulting cis-alkenylcuprate 6 is then reacted with the exo-methylene ketone 1 to yield the cis-alkenyl intermediate 3.

For the preparation of 3-carba prostanoids, the cis-alkenylstannane 4a is of the formula cis-$R"_3SnCH=CH(CH_2)_3Z'$ wherein R" is $C_1$ to $C_6$ alkyl, preferably methyl or n-butyl, and most preferably n-butyl, Z' is a functional group capable of being converted to COOH, and compatible with the conditions of the tin-to-copper transmetalation reaction used to prepare the cis-alkenylcuprate 2a, for example, an ortho ester, acetal, or protected carbinol, as generally known to those skilled in the art. The compound cis-$R"_3SnCH=CH(CH_2)_3Z'$ can be prepared by the general method described by Corey, *Tetrahedron Letters*, volume 25, page 2419 (1984), involving copper-catalyzed coupling of cis-$R"_3SnCH=CHCH_2OAc$ with a Grignard reagent $(Hal)Mg(CH_2)_3Z'$, wherein Hal=Cl, Br or I, and Z' is defined as above.

For the preparation of 3-oxa prostanoids, the cis-alkenylstannane 4b is of the formula cis-$R"_3SnCH=CHCH_2OR'$ wherein R" is defined as above, and R' is a protecting group compatible with the conditions of the tin-to-copper transmetalation reaction used to prepare the cis-alkenylcuprate 2b, for example, substituted silyl, tetrahydropyranyl, or 1-ethoxyethyl. The compound cis-$R"_3SnCH=CHCH_2OR'$ can be prepared by appending a protecting group to cis-$R"_3SnCH=CHCH_2OH$, the preparation of which is known wherein R" is n-butyl; see Corey, above. Alternatively, cis-$R"_3SnCH=CHCH_2OR'$ can be obtained by hydrozirconation of an alkynylstannane; see Lipshutz, *Tetrahedron Letters*, volume 33, page 5861 (1992).

The cis-alpha chain intermediate 3b (generated from the novel methods of the present invention), can be converted to the 3-oxa prostanoids of formula III, wherein A is O, and R, R'R" and ω are defined as above, by employment of known methods in the art, for example, the sequence generally described by Sato, above, and as summarized in Scheme C, below. Accordingly, reduction of the keto group of 3b (wherein X is $CHOSiMe_2t$-Bu (in the R configuration), ω is $CH_2CH_2CH(OSiMe_2t$-Bu$)$-cyclo-$C_6H_{11}$ (in the R configuration), and R' is CH(Me)OEt) gives alcohol 7. Removal of the protecting group CH(Me)OEt, from 7 (by known methods, e.g., Greene et al., *Protective Groups in Organic Synthesis*, $2^{nd}$ ed., Wiley: New York, 1991) gives diol 8. Alkylation of 8 with tert-butyl bromoacetate gives the protected 3-oxa prostanoid 9. The OH group of 9 is substituted, via the methanesulfonate, with chloride to give the protected 9-chloro-3-oxa prostanoid 10. Removal of protecting groups from 10 provides the 9-chloro-3-oxa prostanoid 11. Further processing can be employed to give an analog of 11 containing an alpha chain terminating ester of choice, preferably isopropyl ester.

Scheme C

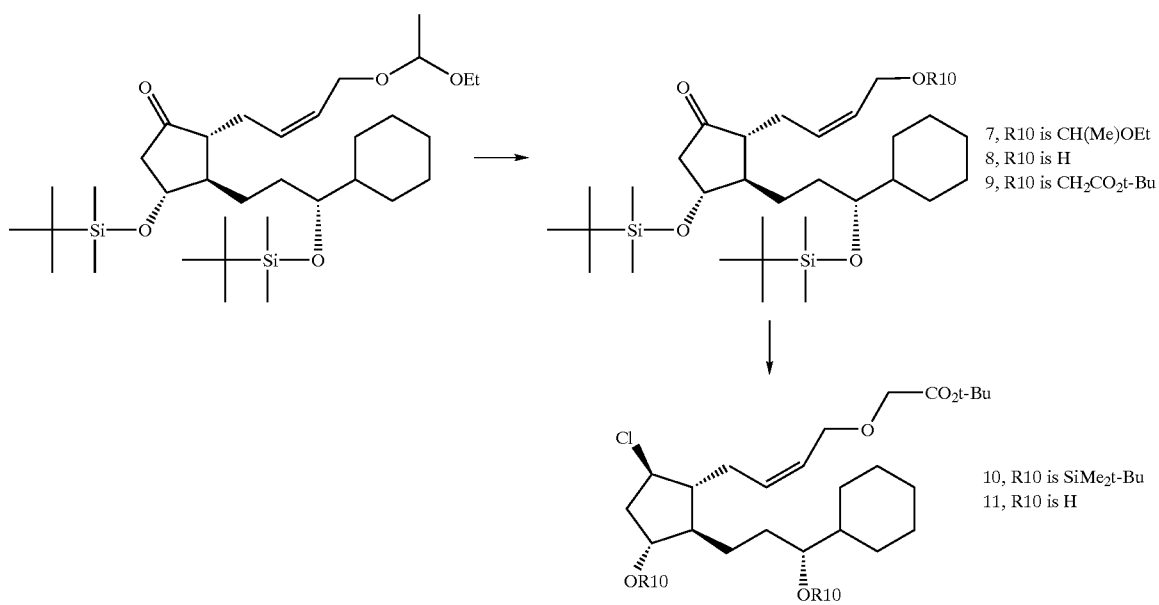

As stated above, the methods of the present invention are also useful in preparing the 3-carba prostanoids of formula III, wherein A is $CH_2$. For example, Stork and Isobe, above, disclose a method of converting a compound of Formula 3a, wherein X is $CHOCH_2Ph$ (in the rel-R configuration), ω is trans-$CH=CHCH(OCH_2OCH_2Ph)C_5H_{11}$ (in the rel-S configuration) and Z' is $CH_2OCH(Me)OEt$, into racemic prostaglandin $F_{2\alpha}$, i.e., the compound of formula III wherein A is $CH_2$, R3 is β-H, α-OH, X is CH—OH (in the rel-R configuration), Q is H and ω is trans-$CH=CHCH(OH)$-n-$C_5H_{11}$ (in the rel-S configuration). A further example is shown in Scheme D. Reduction of the keto group of the compound of formula 3a (wherein X is $CHOSiMe_2t$-Bu (in the R configuration), ω is trans-$CH=CHCH(OSiMe_2t$-Bu) $CH_2OC_6H_4$-m-$CF_3$ (in the R configuration), and Z' is an OBO ester group (see Corey, above) gives alcohol 12. Hydrolysis of the OBO ester group of 12 yields the protected 3-carba prostanoid 13. Removal of protecting groups from 13 yields the free 3-carba prostanoid 14. Further processing can be employed to give an analog of 14 containing an alpha chain terminating ester of choice, preferably, isopropyl ester.

Scheme D

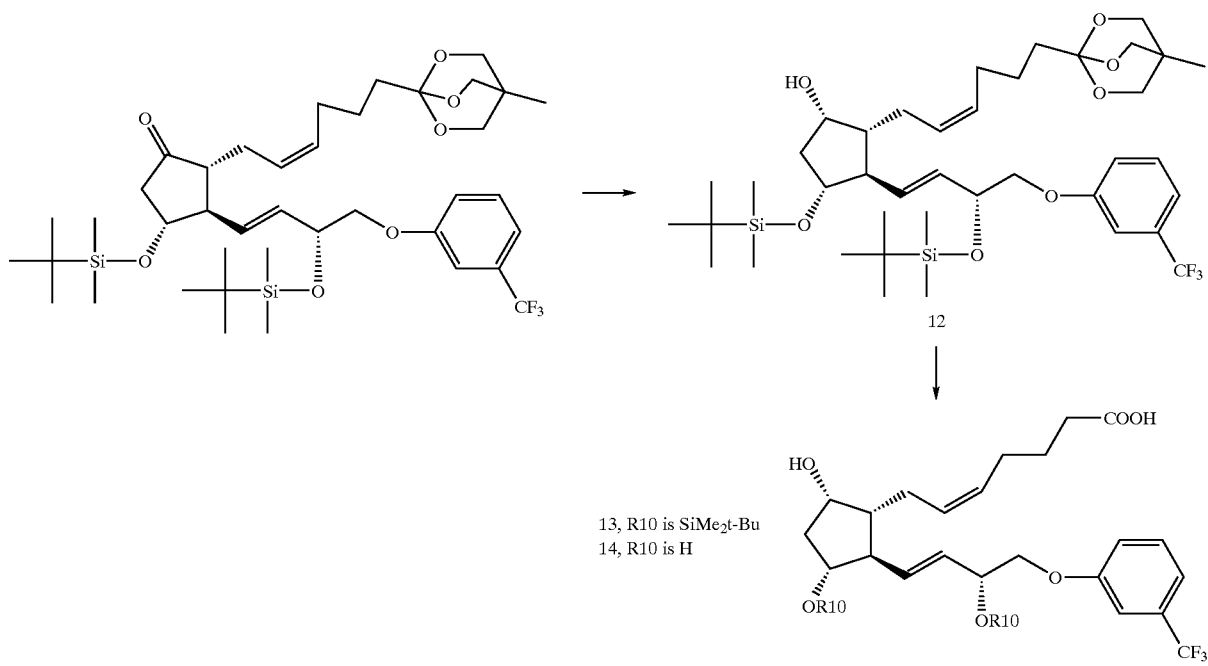

The following example further illustrates a preferred synthesis of the present invention:

EXAMPLE

The following is an example of the present invention: preparation of (2R,3R,4R)-2-[1'-[(2'Z)-4'-[(1-ethoxy) ethoxy]-2'-butenyl]-3-[1'-[(3'R)-3'-(t-butyldimethylsiloxy)-3'-cyclohexyl]-propyl]-4-(t-butyldimethylsiloxy)-cyclopentan-1-one.

Step 1

Preparation of (Z)-Bu$_3$SnCH=CHCH$_2$OCH(Me)OEt. (Z)-Bu$_3$SnCH=CHCH$_2$OH (Corey, above) was reacted with ethyl vinyl ether and catalytic pyridinium p-toluenesulfonate in dichloromethane to give (Z)-Bu$_3$SnCH=CHCH$_2$OCH(Me)OEt. NMR (CDCl$_3$) δ0.9 (m, 9H), 1.21 (t, J=7, 3H), 1.2–1.7 (m, 18H), 1.33 (d, J=5, 3H), 3.4–3.75 (m, 2H), 3.85–4.3 (m, 2H), 4.74 (q, J=5, 1H), 6.07 (1H, d, J=13; Sn satellites (13%), J=74), 6.62 (1H, dt, J=13, 4.3; Sn satellites (13%), J=146).

Step 2

Preparation of (3R,4R)-2-methylene-3-[1'-[(3'R)-3-(t-butyldimethylsiloxy)-3'-cyclohexyl]-propyl]-4-(t-butyldimethylsiloxy)-cyclopentan-1-one.

(a) A solution of 4.25 g (25 mmol) of (R)-3-chloro-1-phenyl-1-propanol in 20 mL of methanol, containing 0.75 g of 5% rhodium-on-alumina, was hydrogenated at 60–65 psig at RT on a Parr shaker for 6.5 hours. The solution was filtered and concentrated, and the crude product was purified by chromatography on silica to give 2.32 g (55%) of (R)-3-chloro-1-cyclohexyl-1-propanol. NMR (DMSO-d$_6$) δ0.8–1.3 (m, 5H), 1.5–1.9 (m, 6H), 3.30 (m, 1H), 3.68 (2 overlapping t, J=5.2 and 7.0, 2H), 4.48 (d, J=5.9, 1H, exchanges).

(b) Ethyl vinyl ether (EVE) (10 mL) was added to a stirred, ice-cooled solution of (R)-3-chloro-1-cyclohexyl-1-propanol (4.89 g, 27.7 mmol) and pyridinium p-toluenesulfonate (PPTS) (0.04 g) in 40 mL of dry CH$_2$Cl$_2$. After 10 minutes, 0.20 g of PPTS and 8 mL of EVE were added, and the solution was allowed to warm to RT. After 1 hour, the solution was filtered through a pad of silica, eluting with diethyl ether. Concentration afforded 6.69 g (97%) of (R)-1-(3-chloro-1-cyclohexyl)propyl (1-ethoxyethyl) ether. NMR (CDCl$_3$) δ0.9–2.0 (m, 13H), 1.21 (t, J=7.0, 3H), 1.30 and 1.32 (2 overlapping d, J=5.3, 3H), 3.4–3.8 (m, 5H), 4.7 (2 overlapping q, J=5.3, 1H).

(c) Lithium wire (1% Na) (68 mg, 9.7 mg-atom) was added in 0.3-cm pieces to a stirred, cooled (0° C. internal) solution of 4,4'-di-t-butylbiphenyl (2.66 g, 10.0 mmol) and 5 mg of 2,2'-bipyridyl in 20 mL of dry tetrahydrofuran (THF) under argon. The mixture was titrated to a red endpoint with n-BuLi (2.5 M in hexane, 0.12 mL) and stirred for 15 hours to form a deep blue-green solution of lithium 4,4'-di-t-butylbiphenyl. The solution was cooled to −45° C. (internal), and a solution of (R)-1-(3-chloro-1-cyclohexyl) propyl(1-ethoxyethyl)ether (1.12 g, 4.5 mmol) in 9.0 mL of dry hexane was added dropwise. After 5 minutes, a solution of 0.25 M lithium (2-thienyl)cyanocuprate in THF (20 mL) was added dropwise. After 10 minutes, a solution of (R)-2-((diethylamino)methyl)-4-(t-butyldimethylsiloxy)-2-cyclopentenone (1.12 g, 3.77 mmol) in 20 mL of dry THF was added dropwise. The solution was allowed to warm to −20° C. and was quenched into a rapidly stirred mixture of diethyl ether and saturated aqueous NH$_4$Cl. After four hours, the layers were separated and the aqueous solution was extracted with ethyl acetate. The combined organic solutions were dried (MgSO$_4$), filtered and concentrated and the crude product was purified by chromatography on silica to give 0.95 g (57.5%) of (3R,4R)-2-methylene-3-[(3'R)-3'-(1-ethoxy)ethoxy)-3'-cyclohexyl-1'-propyl]-4-(t-butyldimethylsiloxy)cyclopentan-1-one. NMR (CDCl$_3$) δ0.06 (s, 3H), 0.08 (s, 3H), 0.87 (s, 9H), 0.8–1.9 (m, 15H), 1.17 and 1.20 (2 overlapping t, J=7, 3H), 1.29 and 1.30 (2 overlapping d, J=5.3, 3H), 2.30 (A of ABX, J$_{ab}$=18.0, J$_{ax}$=4.6, 1H), 2.62 (B of ABX, J$_{ab}$=17.8, J$_{bx}$=5.8, 1H), 2.65 (br s, 1H), 3.30 (br q, J=4, 1H), 3.55 (m, J=6, 2H), 4.12 (pent, J=5.2, 1H), 4.68 (2 overlapping q, J=5.2, 1H), 5.29, 5.32 (both s, 2:3 ratio, total 1H), 6.08 (s, 1H).

(d) Pyridinium p-toluenesulfonate (0.25 g) was added to a stirred solution of 3.2 g (7.3 mmol) of (3R,4R)-2-methylene-3-[(3'R)-3'-(1-ethoxy)ethoxy)-3'-cyclohexyl-1'-propyl]-4-(t-butyldimethylsiloxy)cyclopentan-1-one in 50 mL of diethyl ether and 50 mL of i-PrOH at RT. After 2 hours, the solution was poured into saturated aqueous NaHCO$_3$, and extracted with diethyl ether and ethyl acetate. The combined organic solutions were washed with water and brine, dried (MgSO$_4$), filtered and concentrated. The crude product was purified by chromatography on silica, giving 2.05 g (77%) of (3R,4R)-2-methylene-3-((3'R)-3'-hydroxy-3'-cyclohexyl-1'-propyl)-4-(t-butyldimethylsiloxy)cyclopentan-1-one. NMR (DMSO-d$_6$) δ0.00 (s, 3H), 0.01 (s, 3H), 0.79 (s, 9H), 0.8–1.8 (m, 15H), 2.11 (A of ABX, J$_{ab}$=18.0, J$_{ax}$=4.6, 1H), 2.65 (B of ABX, J$_{ab}$=17.8, J$_{bx}$=5.8, 1H), 2.6 (br s, 1H), 3.10 (br s, 1H), 4.12 (br q, J=5, 1H), 4.21 (d, J=5.5, 1H, exchanges), 5.30 (s, 1H), 5.83 (s, 1H).

(e) To a stirred, ice-cooled solution of 1.53 g (4.2 mmol) of (3R,4R)-2-methylene-3-((3'R)-3'-hydroxy-3'-cyclohexyl-1'-propyl)-4-(t-butyldimethylsiloxy)cyclopentan-1one in 20 mL of dichloromethane and 15 mL of N,N-dimethylformamide under argon was added via syringe N-ethyldiisopropylamine (1.50 mL, 8.6 mmol) followed by t-butyldimethylsiyl triflate (2.0 mL, 8.7 mmol). After 1.5 hours, the mixture was diluted with diethyl ether, extracted with water, then three times with saturated aqueous KH$_2$PO$_4$, water and brine, dried (MgSO$_4$), filtered and concentrated. The crude product was purified by chromatography on silica to give 1.60 g (80%) of (3R,4R)-2-methylene-3-[(3'R)-3'-(t-butyldimethylsiloxy)-3'-cyclohexyl-1'-propyl]-4-(t-butyldimethylsiloxy)cyclopentan-1-one. NMR (CDCl$_3$) δ0.02, 0.03, 0.06, 0.08 (each s, 3H), 0.88 (s, 18H), 0.9–1.8 (m, 15H), 2.30 (A of ABX, J$_{ab}$=18.0, J$_{ax}$=4.6, 1H), 2.62 (B of ABX, J$_{ab}$=17.8, J$_{bx}$=5.8, 1H), 2.63 (br s, 1H), 3.40 (br q, J=5, 1H), 4.09 (q, J=5.7, 1H), 5.28 (d, J=1.5, 1H), 6.08 (d, J=2.2, 1H).

Step 3

Preparation of (2R,3R,4R)-2-[1'-[(2'Z)-4'-[(1-ethoxy) ethoxy]-2'-butenyl]-3-[1'-[(3'R)-3'-(t-butyldimethylsiloxy)-3'-cyclohexyl]-propyl]-4-(t-butyldimethylsiloxy)-cyclopentan-1-one.

Under argon, methyllithium (0.80 mL of a 1 molar solution in 9:1 cumene-tetrahydrofuran) was added dropwise to a stirred, ice-cooled suspension of CuCN powder (36 mg, 0.40 mmol) in 1.0 mL of dry tetrahydrofuran. After 5 min, (Z)—Bu$_3$SnCH=CHCH$_2$OCH(Me)OEt (0.16 g, 0.38 mmol) (from Step 1) was added, rinsing with 0.5 mL of tetrahydrofuran. The solution was allowed to warm to room temperature and was stirred for 1.5 hours, then cooled in a −78° C. bath. A solution of (3R,4R)-2-methylene-3-[1'-[(3'R)-3'-(t-butyldimethylsiloxy)-3'-cyclohexyl]-propyl]-4-(t-butyldimethylsiloxy)-cyclopentan-1-one (0.11 g, 0.23 mmol) (from Step 2) in 0.9 mL of dry tetrahydrofuran was added dropwise. After 10 min, the mixture was poured into saturated aqueous NH$_4$Cl and stirred for several hours. The phases were separated and the aqueous solution was extracted with ethyl acetate. The combined organic solutions were dried over MgSO$_4$, filtered and concentrated, and the crude product was purified by chromatography on silica to afford 0.10 g (72%) of (2R,3R,4R)-2-[1'-[(2'Z)-4'-[(1-ethoxy)ethoxy]-2'-butenyl]-3-[1'-[(3'R)-3'-t-butyldimethylsiloxy)-3'-cyclohexyl]-propyl]-4-(t-butyldimethylsiloxy)-cyclopentan-1-one. NMR (CDCl$_3$): δ0.02, 0.03, 0.05, 0.08 (each s, 3H), 0.89 (s, 18H), 0.9–1.8 (m, 15H), 1.21 (t, J=7.0, 3H), 1.31 (t, J=5.3, 3H), 1.9 (br s, 2H), 2.15 (A of ABX, Jab18.0, Jax=4.6, 1H), 2.59 (B of ABX, Jab=17.8, Jbx=5.8, 1H), 2.42 (br t, J=5.7, 2H), 3.39 (br q, J=5, 1H), 3.6 (m, 2H), 4.1 (m, 3H), 4.72 (q, J=5.3, 1H), 5.6 (m, 2H).

The (2R,3R,4R)-2-[1'-[(2'Z)-4'-[(1-ethoxy)ethoxy]-2'-butenyl]-3-[1'-[(3'R)-3'-(t-butyldimethylsiloxy)-3'-cyclohexyl]-propyl]-4-(t-butyldimethylsiloxy)-cyclopentan-1-one product of the above Example can now be used in various prostanoid syntheses known to those skilled in the art. For example, the product may be inserted in Scheme C or D for the preparation of 3-oxa or 3-carba prostanoids, respectively. Other examples of prostanoid synthesis for which the product would be a useful intermediate include methods disclosed in commonly assigned U.S. patent application Ser. No. 08/167,470, filed Dec. 15, 1993.

By employment of known methods in the art, for example, the sequence generally described by Sato, above, the (2R,3R,4R)-2-[1'-[(2'Z)-4'-[(1-ethoxy)ethoxy]-2'-butenyl]-3-[1'-[(3'R)-3'-(t-butyldimethylsiloxy)-3'-cyclohexyl]-propyl]-4-(t-butyldimethylsiloxy)-cyclopentan-1-one product of the above Example can be converted to (5Z)-(9R,11R,15R)-9-chloro-15-cyclohexyl-11,15-dihydroxy-3-oxa-16,17,18,19,20-pentanor-5-prostenoic acid.

I claim:

1. A method for preparing prostanoids of formula (III)

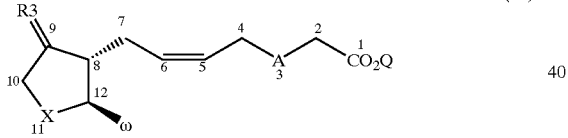

(III)

wherein,
X is O, CH$_2$, C=O, or CH—OR$^4$ in either configuration, or CH-halogen (F, Cl, Br, I) in either configuration;
A is O;
Q is H or C$_{1-4}$ alkyl;
R3 is H and one of: H, OR$^4$, halogen, in either configuration, or, R3 is O;
R$^4$ is H, alkyl, acyl, or Si(R$^6$)$_3$, wherein R$^6$ is independently C$_{1-4}$ alkyl or phenyl;
provided that when R3 is O, X is not CH-halogen, and when R3 is H and halogen, X is not C=O;
ω is

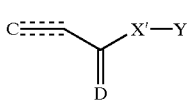

wherein:
---- is an optional bond;
D is H and one of: H, F or OR$^4$, in either configuration; or D is O;

X' is (CH$_2$)$_m$ or (CH$_2$)$_m$O, wherein m is 1 to 6; or X' is CH—OH; and

Y is a phenyl ring optionally substituted with alkyl, halo, trihalomethyl, alkoxy, acyl, acyloxy, amino, alkylamino, acylamino, or hydroxy; or Y is C$_{1-6}$ alkyl or C$_{3-8}$ cycloalkyl, optionally substituted with C$_{1-6}$ alkyl, or X'—Y is (CH$_2$)$_p$Y'; wherein p is 0 to 6; and

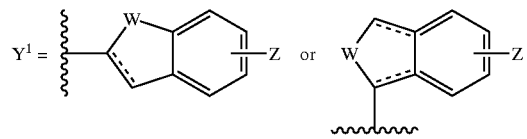

wherein:

W is CH$_2$, O, S(O)$_q$, NR$^5$, CH$_2$CH$_2$, CH=CH, CH$_2$O, CH$_2$S(O)$_q$, CH=N, or CH$_2$NR$^5$;

wherein q is 0 to 2, and R$^5$ is H, alkyl, or acyl;

Z is H, alkyl, alkoxy, acyl, acyloxy, halo, trihalomethyl, amino, alkylamino, acylamino, or hydroxy; and ---- is an optional bond; or X$^1$—Y is C$_{1-6}$ alkyl, or C$_{3-8}$ cycloalkyl, comprising the steps of:

(a) reacting a compound of formula (IV):

(IV)

wherein, R$^{11}$ is C$_1$–C$_6$ alkyl and R$^1$ is alkyl, arylalkyl, alkoxyalkyl or substituted silyl, with a compound of formula (V):

(V)

wherein R is C$_1$–C$_6$ alkyl, to form a product of formula (VI):

(VI)

(b) reacting the product (VI) with a compound of the formula (VII):

(VII)

to form a compound of formula (III), wherein is A is O.

2. A method for preparing 3-carba prostanoids of formula (III):

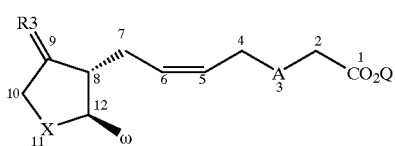
(III)

wherein,

X is O, $CH_2$, C=O, or CH—$OR^4$ in either configuration, or CH-halogen (F, Cl, Br, I) in either configuration;

A is $CH_2$;

Q is H or $C_{1-4}$ alkyl;

R3 is H and one of: $OR^4$, halogen, H, in either configuration, or, R3 is O;

$R^4$ is H, alkyl, acyl, or $Si(R^6)_3$, wherein $R^6$ is independently $C_{1-4}$ alkyl or phenyl;

with the proviso that if R3 is O then X is not CH-halogen, and that if R3 is CH-halogen then X is not C=O;

ω is

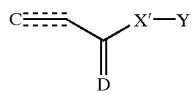

wherein:

---- is an optional bond;

D is H and one of: H, F or $OR^4$, in either configuration; or D is O;

X' is $(CH_2)_m$ or $(CH_2)_mO$, wherein m is 1 to 6; or X' is CH—OH; and

Y is a phenyl ring optionally substituted with alkyl, halo, trihalomethyl, alkoxy, acyl, acyloxy, amino, alkylamino, acylamino, or hydroxy; or Y is $C_{1-6}$ alkyl or $C_{3-8}$ cycloalkyl, optionally substituted with $C_{1-6}$ alkyl, or X'—Y is $(CH_2)_pY'$; wherein p is 0 to 6; and

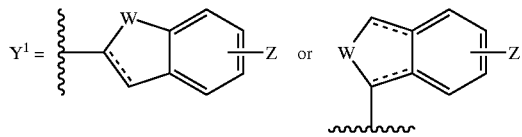

wherein:

W is $CH_2$, O, $S(O)_q$, $NR^5$, $CH_2CH_2$, CH=CH, $CH_2O$, $CH_2S(O)_q$, CH=N, or $CH_2NR^5$;

wherein q is 0 to 2, and $R^5$ is H, alkyl, or acyl;

Z is H, alkyl, alkoxy, acyl, acyloxy, halo, trihalomethyl, amino, alkylamino, acylamino, or hydroxy; and ---- is an optional bond; or $X^1$—Y is $C_{1-6}$ alkyl, or $C_{3-8}$ cycloalkyl, comprising the steps of:

(a) reacting a compound of formula (VIII):

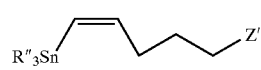
(VIII)

wherein, $R^{11}$ is $C_{1-6}$ alkyl and $Z^1$ is $CH_2OR^1$, $CH(O-alkyl)_2$ or $C(O-alkyl)_3$, and $R^1$ is alkyl, arylalkyl, alkoxyalkyl or substituted silyl, with a compound of formula (V):

(V)

wherein R is $C_{1-6}$ alkyl, to form a product of formula (IX):

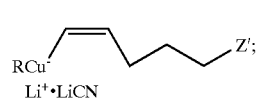
(IX)

(b) reacting the product (IX) with a compound of the formula (VII):

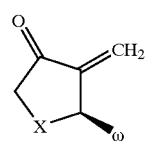
(VII)

to form a compound of formula (III), wherein A is $CH_2$.

* * * * *